(12) United States Patent
Bartee et al.

(10) Patent No.: US 10,589,004 B2
(45) Date of Patent: Mar. 17, 2020

(54) MATERIALS FOR SOFT AND HARD TISSUE REPAIR

(71) Applicant: OBI BIOLOGICS, INC., Lubbock, TX (US)

(72) Inventors: Barry K. Bartee, Lubbock, TX (US); Richard A. Rosen, Lubbock, TX (US)

( * ) Notice: Subject to any disclaimer, the term of this patent is extended or adjusted under 35 U.S.C. 154(b) by 325 days.

(21) Appl. No.: 15/445,955

(22) Filed: Feb. 28, 2017

(65) Prior Publication Data

US 2017/0232154 A1    Aug. 17, 2017

Related U.S. Application Data

(63) Continuation of application No. 13/406,424, filed on Feb. 27, 2012, now abandoned.

(60) Provisional application No. 61/446,956, filed on Feb. 25, 2011, provisional application No. 61/515,803, filed on Aug. 5, 2011.

(51) Int. Cl.
| | | |
|---|---|---|
| *A61L 31/00* | (2006.01) | |
| *A61L 27/24* | (2006.01) | |
| *A61L 27/50* | (2006.01) | |
| *A61L 27/38* | (2006.01) | |
| *A61L 27/54* | (2006.01) | |
| *A61L 27/34* | (2006.01) | |
| *A61F 2/00* | (2006.01) | |
| *A61L 31/04* | (2006.01) | |
| *A61L 31/14* | (2006.01) | |
| *A61L 31/16* | (2006.01) | |

(52) U.S. Cl.
CPC .......... *A61L 31/005* (2013.01); *A61F 2/0063* (2013.01); *A61L 27/24* (2013.01); *A61L 27/34* (2013.01); *A61L 27/38* (2013.01); *A61L 27/50* (2013.01); *A61L 27/54* (2013.01); *A61L 31/044* (2013.01); *A61L 31/14* (2013.01); *A61L 31/16* (2013.01); *A61L 2300/414* (2013.01); *A61L 2300/608* (2013.01); *A61L 2430/02* (2013.01); *A61L 2430/34* (2013.01)

(58) Field of Classification Search
CPC ...... A61F 2/0063; A61L 27/24; A61L 31/044; A61L 2300/608; A61L 2430/34
See application file for complete search history.

(56) References Cited

U.S. PATENT DOCUMENTS

| | | |
|---|---|---|
| 5,711,969 A | 1/1998 | Patel et al. |
| 5,837,278 A | 11/1998 | Geistlich et al. |
| 6,420,119 B1 * | 7/2002 | Polan ............... A61K 38/57 |
| | | 435/6.16 |

(Continued)

OTHER PUBLICATIONS

Axer et al., Collagen Fibers in Linea Alba and Rectus Sheaths I. General Scheme and Morphological Aspects 2001, Journal of Surgical Research, 96, 127-134.*

(Continued)

*Primary Examiner* — Diane D Yabut
(74) *Attorney, Agent, or Firm* — Loza & Loza, LLP; Anthony G. Smyth

(57) ABSTRACT

Biomaterials and methods and uses for repair or augmentation of tissues are provided. In particular, the invention provides a multi-layered, naturally occurring multi-axial oriented biomaterial comprising predominately type I collagen fibers. The invention further provides methods and uses for repair or augmentation of tissues using biomaterials of the invention.

24 Claims, 17 Drawing Sheets

(56) References Cited

U.S. PATENT DOCUMENTS

| | | |
|---|---|---|
| 6,482,231 B1 | 11/2002 | Abatangelo et al. |
| 6,514,515 B1 | 2/2003 | Williams |
| 2002/0143234 A1 | 10/2002 | Lovuolo |
| 2006/0140915 A1 | 6/2006 | Schatz et al. |
| 2006/0159665 A1 | 7/2006 | Giannetti |
| 2007/0027535 A1 | 2/2007 | Purdy, Jr. et al. |
| 2008/0286268 A1 | 11/2008 | Johnson |
| 2010/0028396 A1 | 2/2010 | Ward et al. |
| 2010/0074874 A1 | 3/2010 | Torbet et al. |

OTHER PUBLICATIONS

Jarman-Smith et al., Porcine collagen crosslinking, degradation and its capability for fibroblast adhesion and proliferation, 2004, J Mater Sci Mater Med., 15(8), 925-932 (Year: 2004).*

Deeken et al. "Physiomechanical evaluation of polypropylene, polyester and polytetrafluoroethylene meshes for inguinal hernia repair." J. Am. Coll. Surg, 212:68-79 (2011).

Levi et al. "Transplantation of the abdominal wall." Lancet 361(9376):2173-6 (203).

De Vries, et al., "Autologous tissue repair of large abdominal wall defects." B. J. Surg. 94(7):791-803 (2007).

Deeken et al. "Differentiation of biologic scaffold materials through physomechanical, thermal and enzymatic degradation techniques." Annals of Surgery 00(00):1-10 (2012).

Deeken et al. "Physicomechanical evaluation of absorbable and nonabsorbable barrier composite meshes for laparoscopic ventral hernia repair." Surg. Endosc. 25:1451-1552 (2010).

Gondolesi et al. "Use of abdominal rectus fascia as a nonvascularized allograft for abdominal wall closure after liver, intestinal and multivisceral transplantation." Transplantation 87(12):1884-8 (2009).

PCT/US2012/026813. Int'l Preliminary Report on Patentability (dated Sep. 6, 2013).

* cited by examiner

THICKNESS (mm):

|  | ABS-1 | ABS-2 | ABS-3 | ABS-4 | ABS-5 | ABS-6 | Overall |
|---|---|---|---|---|---|---|---|
| N = | 9 | 9 | 9 | 9 | 9 | 9 | 54 |
| Mean | 3.42 | 2.93 | 2.08 | 3.05 | 2.18 | 2.25 | 2.65 |
| Std Dev | 0.6 | 0.8 | 0.6 | 0.9 | 0.7 | 0.4 | 0.8 |
| SEM | 0.2 | 0.3 | 0.2 | 0.3 | 0.2 | 0.1 | 0.1 |

SUTURE RETENTION (N):

|  | ABS-1 | ABS-2 | ABS-3 | ABS-4a | ABS-4b | ABS-6 | Overall |
|---|---|---|---|---|---|---|---|
| N = | 1 | 1 | 1 | 1 | 1 | 1 | 6 |
| Mean | 50.40 | 53.46 | 37.02 | 30.47 | 66.27 | 57.99 | 49.27 |
| Std Dev | 0.0 | 0.0 | 0.0 | 0.0 | 0.0 | 0.0 | 13.3 |
| SEM | 0.0 | 0.0 | 0.0 | 0.0 | 0.0 | 0.0 | 5.4 |

TEAR RESISTANCE (N):

|  | ABS-1 | ABS-2 | ABS-3 | ABS-4 | ABS-5 | ABS-6 | Overall |
|---|---|---|---|---|---|---|---|
| N = | 1 | excluded | 1 | 1 | 1 | 1 | 5 |
| Mean | 16.97 | from | 19.99 | 35.90 | 38.03 | 20.26 | 26.23 |
| Std Dev | 0.0 | analysis | 0.0 | 0.0 | 0.0 | 0.0 | 9.9 |
| SEM | 0.0 |  | 0.0 | 0.0 | 0.0 | 0.0 | 4.4 |

BALL BURST - MAX LOAD (N):

|  | ABS-1 | ABS-2 | ABS-3 | ABS-4 | ABS-5 | ABS-6 | Overall |
|---|---|---|---|---|---|---|---|
| N = | 1 | 1 | excluded | 1 | 1 | 1 | 5 |
| Mean | 493.60 | 463.00 | from | 767.80 | 755.20 | 1022.00 | 700.30 |
| Std Dev | 0.0 | 0.0 | analysis | 0.0 | 0.0 | 0.0 | 229.1 |
| SEM | 0.0 | 0.0 |  | 0.0 | 0.0 | 0.0 | 102.5 |

BALL BURST - TENSILE STRENGTH (N/cm):

|  | ABS-1 | ABS-2 | ABS-3 | ABS-4 | ABS-5 | ABS-6 | Overall |
|---|---|---|---|---|---|---|---|
| N = | 1 | 1 | excluded | 1 | 1 | 1 | 5 |
| Mean | 139.00 | 99.93 | from | 259.40 | 153.80 | 285.70 | 187.60 |
| Std Dev | 0.0 | 0.0 | analysis | 0.0 | 0.0 | 0.0 | 80.6 |
| SEM | 0.0 | 0.0 |  | 0.0 | 0.0 | 0.0 | 36.0 |

BALL BURST - STRAIN AT 16N/cm (%):

|  | ABS-1 | ABS-2 | ABS-3 | ABS-4 | ABS-5 | ABS-6 | Overall |
|---|---|---|---|---|---|---|---|
| N = | 1 | 1 | excluded | 1 | 1 | 1 | 5 |
| Mean | 24.80 | 13.00 | from | 18.42 | 9.84 | 9.03 | 15.02 |
| Std Dev | 0.0 | 0.0 | analysis | 0.0 | 0.0 | 0.0 | 6.6 |
| SEM | 0.0 | 0.0 |  | 0.0 | 0.0 | 0.0 | 3.0 |

Fig. 10(b)

MATERIALS FOR SOFT AND HARD TISSUE REPAIR

PRIORITY CLAIM

This application is a continuation of copending U.S. application Ser. No. 13/406,424, which claims priority from U.S. Provisional Application No. 61/446,956, filed on Feb. 25, 2011, and U.S. Provisional Application No. 61/515,803, filed on Aug. 5, 2011, the entire content of which applications are incorporated herein by reference as if fully set forth below in its entirety and for all applicable purposes.

TECHNICAL FIELD

The invention relates to biomaterials and methods and uses for tissue repair or augmentation.

INTRODUCTION

Collagen rich, naturally derived tissue has been used to repair hernias and large abdominal wall defects for many years. The use of autologous human fascia lata to repair hernia defects was reported by Kirschner in 1913. Fascia lata, a dense layer of collagen rich connective tissue, was taken from a donor site on the lateral (outside) aspect of the thigh along with the accompanying blood vessels, and transplanted to the defect. This type transplant, with the patient being both the donor and recipient, is known as an autologous transplant. If there are no blood vessels brought with the tissue and where circulation is re-established by connection of the blood vessels, it is known as a "free graft" or transplant. If the blood vessels are brought along, and reconnected, it is known as a "vascularized graft" or transplant. A major disadvantage to this type of procedure however, in addition to the large surgical procedure required to harvest the tissue, is the risk donor site morbidity such as lateral knee instability. Indeed, studies indicate that this procedure has a high post operative complication rate in the range of 10% to 40%. Recurrent hernia occurred in 10 to 25% of patients followed for up to 29 months using this procedure. One possible reason for the failure in this technique is that autologous tissues, especially if not vascularized, can be readily resorbed. The inherent limitations of autologous tissues for soft tissue repair led to the development and widespread use of synthetic prosthetic mesh materials for hernia and abdominal wall defect repair.

There may as many as 5 million laparotomies performed yearly in the United States, and approximately 20% result in incisional hernias. Approximately a quarter of a million ventral incisional hernias are repaired annually. These figures do not take into account other hernias such as femoral, inguinal umbilical, parastomal, hiatal, diaphragmatic and Spigelian. Prosthetic mesh repair, instead of suture alone, reduces recurrence risk by approximately 50%.

Synthetic hernia repair meshes for many years have represented the Gold Standard for surgical repair. The so-called "heavyweight" synthetic meshes represent the first generation of products. These products are not without their problems, which include infection, scar formation and pain, adhesion formation with viscera leading to bowel obstruction and fistula. These problems have lead to the development of a variety of synthetic and biologic materials for repair of soft tissue defects, weaknesses, hernias or inadequacies. Currently, several synthetic meshes including polypropylene (prolene), polyester and polytetrafluoroethylene (PTFE) are used. Some of these polymers have recently been manufactured in combination with a variety of partially absorbable coatings, designed to limit adhesion formation and the attendant complications. In addition, it has become evident that strength alone is not the most important feature in a hernia mesh, but rather the flexibility and compliance with the body wall are important as well. In an attempt to alleviate some of the problems associated with the "heavyweight" synthetics, so-called "lightweight" synthetic meshes have been introduced. These typically have reduced tensile strength compared to heavyweight mesh, but have increased flexibility and greater compliance, with the biomechanical characteristics closer to the abdominal wall.

The drawbacks associated with the synthetic meshes (both heavyweight and lightweight) have lead to the development of "biologic" meshes. These products are derived from tissues such as acellular human dermal matrix, acellular animal (porcine or bovine) dermal matrix, as well as from porcine small bowel submucosa. A major advantage of the biologic meshes compared to the synthetics is a reduction in the risk of post-operative infection, reduced bowel adhesions and/or fistula formation. However, once in widespread use, the biologics have been shown to have their own drawbacks: namely laxity and recurrence of hernia over time. Over the past few years, the problems with these materials have become apparent and re-operation for secondary repair has been required in some cases. To address these issues, it would be advantageous to have a biologic hernia repair material with the advantages and properties of the current biologic meshes, namely a reduction in infection risk and reduction of adhesion risk, while simultaneously possessing the biomechanical advantages and properties of the current synthetic meshes.

An adjunctive technique to repair hernias large abdominal wall defects include the use of component separation (CST). In CST, the muscle and fascia layers of the patient's abdominal wall are separated by dissection and in some cases transection of the muscle and fascial layers, and the muscle layers and/or fascial layers are advanced toward the midline to close large abdominal wall defects. While CST may be used alone to achieve closure, it also may be used in conjunction with synthetic or natural prosthetic patch materials to not only increase the ability to close large defects, but also to reduce tension on the closure, leading to decreased risk for recurrence.

SUMMARY

The invention provides a multi-layered, naturally occurring multi-axial oriented biomaterial comprising predominately type I collagen fibers, wherein the biomaterial is suitable for tissue repair or augmentation. The invention further provides methods and uses for repair or augmentation of a tissue of a recipient mammalian subject (mammalian or non-mammalian) in need of repair or augmentation utilizing the biomaterial of the invention. The invention yet further provides methods and uses for manufacture of a biomaterial suitable for tissue repair or augmentation.

BRIEF DESCRIPTION OF THE DRAWINGS

FIGS. 10(a) and 10(b) show ball burst testing results of an exemplary bovine fascia biomaterial according to the invention.

DETAILED DESCRIPTION

Figure 1A:
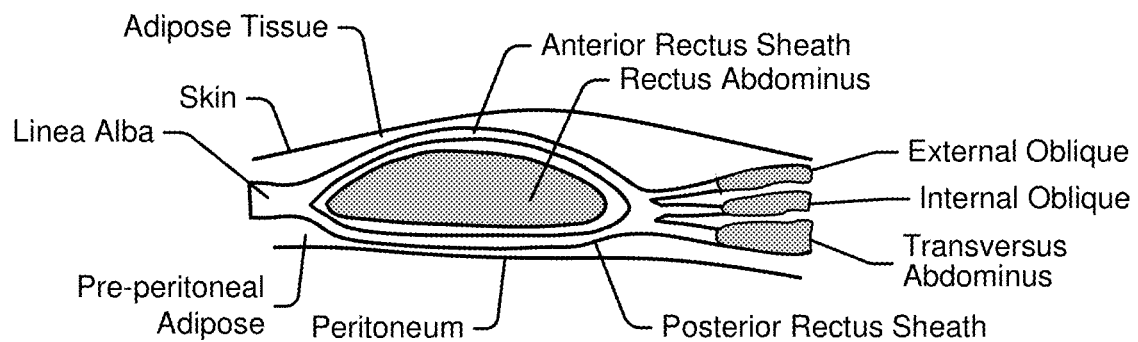
FIGS. 1(a) and (b) illustrate the muscle and fascial layers of the human abdominal wall: (a) illustrates the abdominal wall above the arcuate line, where the vertically oriented rectus abdominus is covered anteriorly and posteriorly by fascia consisting of a combination of all three distinct muscle layers namely the external oblique, the internal oblique, and the transversus abdominis; and (b) illustrates the abdominal wall below the arcuate line, where the rectus abdominus muscle is covered anteriorly only by fascia, thereby making a very dense, strong connective tissue layer with fibers oriented in multiple directions.

The invention provides biomaterials, and methods and uses of biomaterials for tissue repair or augmentation. Invention biomaterials are suitable for repair or augmentation of soft or hard tissues, such as abdominal wall, muscle, orthopedic applications, etc. The biomaterial is a naturally occurring, multi-layered and multi-axial oriented containing predominately collagen, e.g., type I collagen. The term "collagen" as used herein refers to all forms of collagen, including those which have been processed or otherwise modified. Optionally, the type I collagen fibers may be multi-axial oriented. In certain embodiments, the biomaterial is multi-laminar. In certain embodiments, the biomaterial is multi-directional with regard to fiber orientation of the collagen fibers. For example, the fibers have a multi-directional (axial) orientation, and all fibers are not all parallel to each other. The multi-directional (axial) fiber orientation provides additional strength to the biomaterial. In various embodiments, the interdigitation of the collagen fibers are arranged at angles, such as between 1 and 359 degrees relative to another fibers, for example, between 45 and 90 degrees relative to one another.

In various embodiments, the biomaterial is derived from a mammalian source or a non-human source, such as a porcine, a bovine, an ovine, an equine, a hircine, or any suitable mammal source. In certain embodiments, the biomaterial includes a multi-density construct derived from one or more of dermis, rectus sheath fascia (e.g., rectus abdominis fascia), shoulder, hind and/or forequarter tissues. In certain embodiments, the biomaterial is derived from dense fibrous, aponeurotic layers of a mammalian body or non-human body or tissue source, for example, an oriented fibrous structure of fascia (i.e., porcine rectus sheath, bovine forequarter fascia), or fascia lata. In certain embodiments, the biomaterial includes connective tissue, which comprises a collagen scaffold, optionally free of muscle cells.

The biomaterial is intended to mimic one or more of physiomechanical, biomechanical, and/or anatomical properties of a natural tissue. The mammalian or non-human body or tissue source may mimic the architecture and physiomechanical characteristics of the tissue being repaired, for example, the abdominal wall of a mammal, human or non-human body. In certain embodiments, the mammalian or non-human body or tissue source may mimic a connective tissue, or naturally oriented fibers of the abdominal wall (e.g., anterior abdominal wall) of a mammal, human or non-human body. In certain embodiments, the biomaterial is constructed of multiple layers of tendinous, aponeurotic fibrous collagen from diverse mammalian tissue sources forming diverse tissue construct mimicking the naturally oriented fibers of the anterior abdominal wall. As such, the biomaterial may exhibit various properties of an abdominal wall. The biomaterial may mimic the composition and structure of an abdominal wall. The biomaterial may conform to the abdominal wall anatomy.

Anatomy of the Abdominal Wall

The intact rectus sheath consists of multiple layers of strong, dense, fibrous fascial layers of primarily type I collagen which eventually encircle the central muscular pillar of the abdomen, the rectus abdominis muscle. Moreover, these musculofascial layers of the anterior abdominal wall are oriented in three separate and distinct directions with respect to the midline of the abdomen, an arrangement designed to withstand loading from multiple directions.

The external oblique muscle is the outermost muscular layer. It originates from the lower aspect of the ribs and courses inferio-medially where it forms a fibrous aponeurosis and attaches at the linea alba. Both of the external oblique aponeurotic laminae course anterior to the rectus abdominis muscle above and below the arcuate line. These aponeurotic fibers of the external oblique are oriented at 45 degrees with respect to the vertical midline.

Figure 1B:
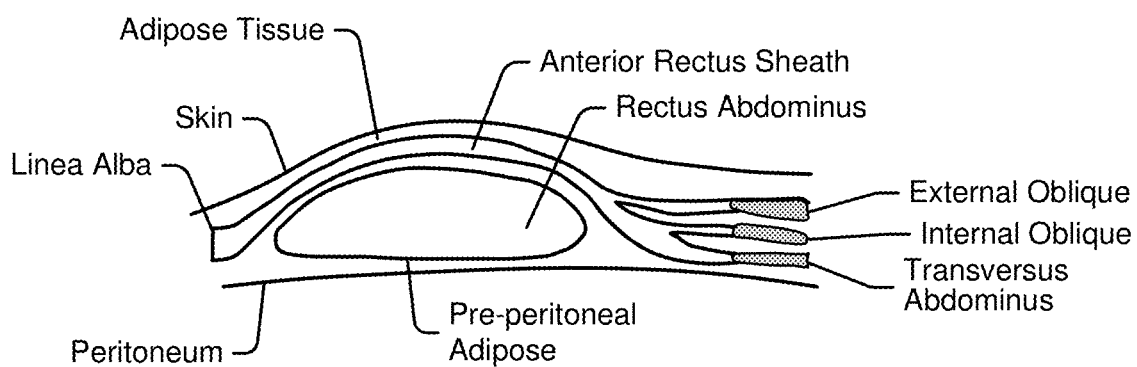

The internal oblique musculofascial layer originates from the anterior iliac crest, the inguinal ligament and the posterior aponeurosis of the transversus abdominis muscle. The musculotendinous fibers of the internal oblique run superiomedially at a 90 degree angle to the external oblique layer, inserting on the cartilages of the lower ribs. At the lateral border of the rectus abdominis muscle and above the arcuate line, the aponeurosis of the internal oblique splits into two laminae, one course anterior to the rectus abdominis, the other laminae posterior, encircling the rectus abdominis muscle, contributing to both the anterior and posterior rectus sheaths (FIG. 1a). Below the arcuate line, the internal oblique aponeurosis does not split, and both laminae course anteriorly along with both laminae of the transversus abdominis forming the anterior rectus sheath (FIG. 1b). The inferior aponeurotic fibers then pass beneath the spermatic cord, pass through the inguinal canal and descend posterior to the superficial ring to attach to the pubic crest. The most inferior fibers of the aponeurosis fuse with the aponeurosis of the transversus abdominis to form the conjoint tendon, which courses inferiorly to insert on the pubic crest.

The innermost layer, the transverse abdominis layer, runs horizontally at a 90 degree angle with respect to the midline, intersecting the external and internal oblique layers at a 45 degree angle. This muscle originates at the iliac crest and inguinal ligament inferiorly, the inner surface of the lower costal cartilages superiorly and has a fibrous origin from the transverse processes of the lumbar vertebra bilaterally. These fibers all run medially to insert at the lateral border of the rectus muscle. Above the arcuate line, the insertion forms an aponeurosis, contributing to the posterior rectus sheath.

The rectus muscles are vertically oriented, paired muscles forming the principle vertical muscle column of the anterior abdominal wall. Inferiorly, the rectus muscle originates from the pubic symphysis and pubic crest. It inserts superiorly on the xiphoid process and the costal cartilages of the lower ribs. The lateral border of each rectus and its sheath merge with the aponeurosis of the external oblique muscle laterally to form the linea semilunaris, a dense collection of tendinous fibers running vertically at the lateral border of the rectus sheath. Toward the midline, the aponeurotic layers coalesce forming another dense vertical teninous band of collagen, the linea alba, Due to the unique and optimal orientation of the collagen fibers within these fascial layers and in conjunction with the associated paired muscles, the intact abdominal wall provides core strength protection to vital organs, as well as stabilizes and facilitates movement and posture of the trunk.

In the invention, suitable fascia may be harvested either above or below the arcuate line of an abdominal wall of a mammalian or non-human source.

Figure 2:
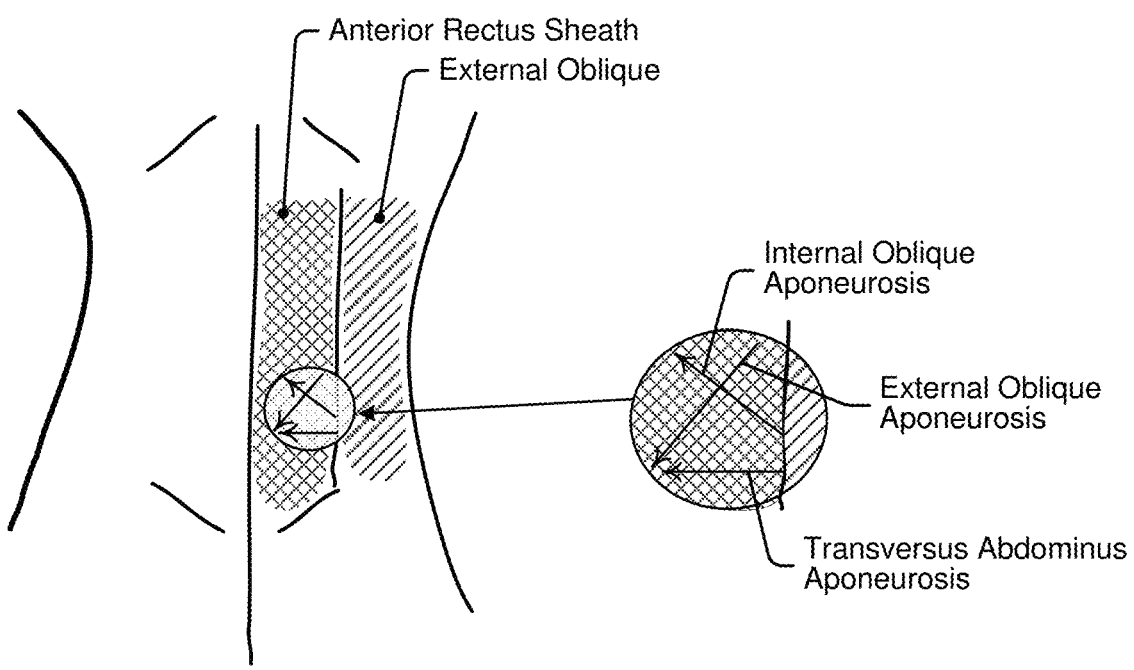
FIG. 2 shows the rectus fascia fiber orientation of a human abdominal wall.

The rectus fascia fiber orientation of a human abdominal wall is shown in FIG. 2. The three layers, namely internal oblique aponeurosis, external oblique aponeurosis and transversus abdominus aponeurosis, are enlarged on the right hand side of the figure showing that the fiber structures are oriented at right angles to one another. When a hernia occurs, a defect occurs in one or more of these layers. To repair a hernia defect, a material must be strong enough to withstand intraabdominal pressure and the forces applied to the abdominal wall tissue during everyday activity.

The invention employs a fascia, either from the abdominal wall of a mammalian or non-human source such as a pig, or a cow (e.g. the shoulder region of a cow), or a horse. The rectus fascia fiber orientation of the abdominal wall of a mammlian or non-human is similar in architecture as that of the human. These fascial tissues are decellularized and optionally freeze-dried prior to implantation to reduce antigenicity, serving as a biological implant with fiber architecture and orientation similar to the tissue that is being repaired.

Certain embodiments of the invention provide a biomaterial derived from a mammalian or a non-human fascia. Fascia is composed of strong, thick collagen fibers aligned along lines of stress similar to the human abdominal wall. Unlike dermis, it composes of smaller, randomly oriented collagen fibers. For comparison and illustration purposes, Scanning Electron Microscopy (SEM) was conducted on scaffolds of porcine fascia, bovine fascia and porcine dermis, and the SEM images are shown in FIGS. 3(a)-(f).

Figure 3A:
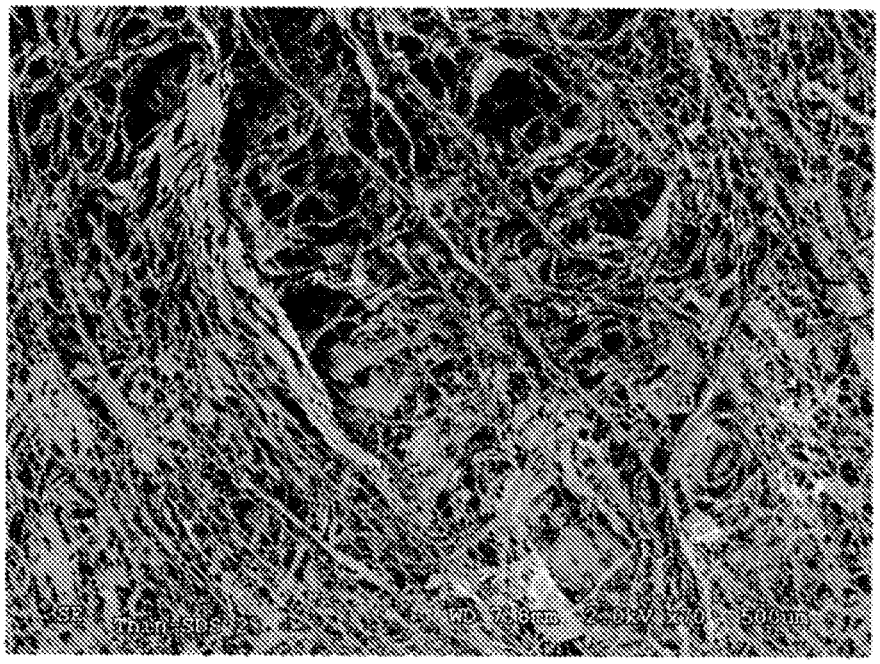
FIGS. 3(a) to (f) are SEM photographs of decellularized and lyophilized biomaterial obtained as described herein showing (a) porcine rectus sheath fascia surface, (b) porcine rectus sheath fascia cross-sectional view, (c) bovine shoulder fascia collagen surface view, (d) porcine dermis surface, (e) bovine shoulder fascia layers (100× magnification), (f) bovine shoulder fascia layers (250× magnification), and (g) bovine shoulder fascia collagen with H&E stained sections (40× and 100× magnifactions).
Figure 3B:
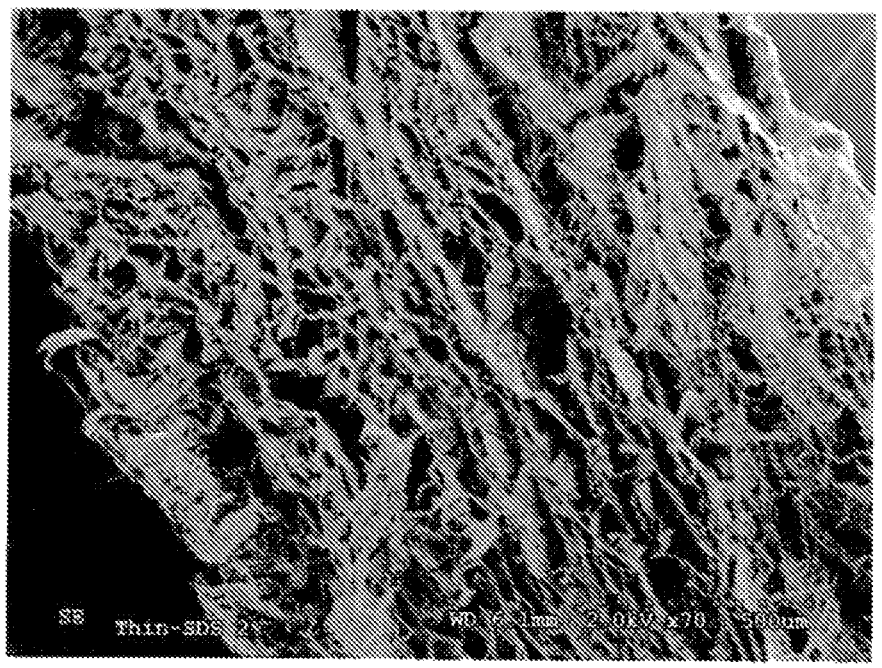
Figure 3C:
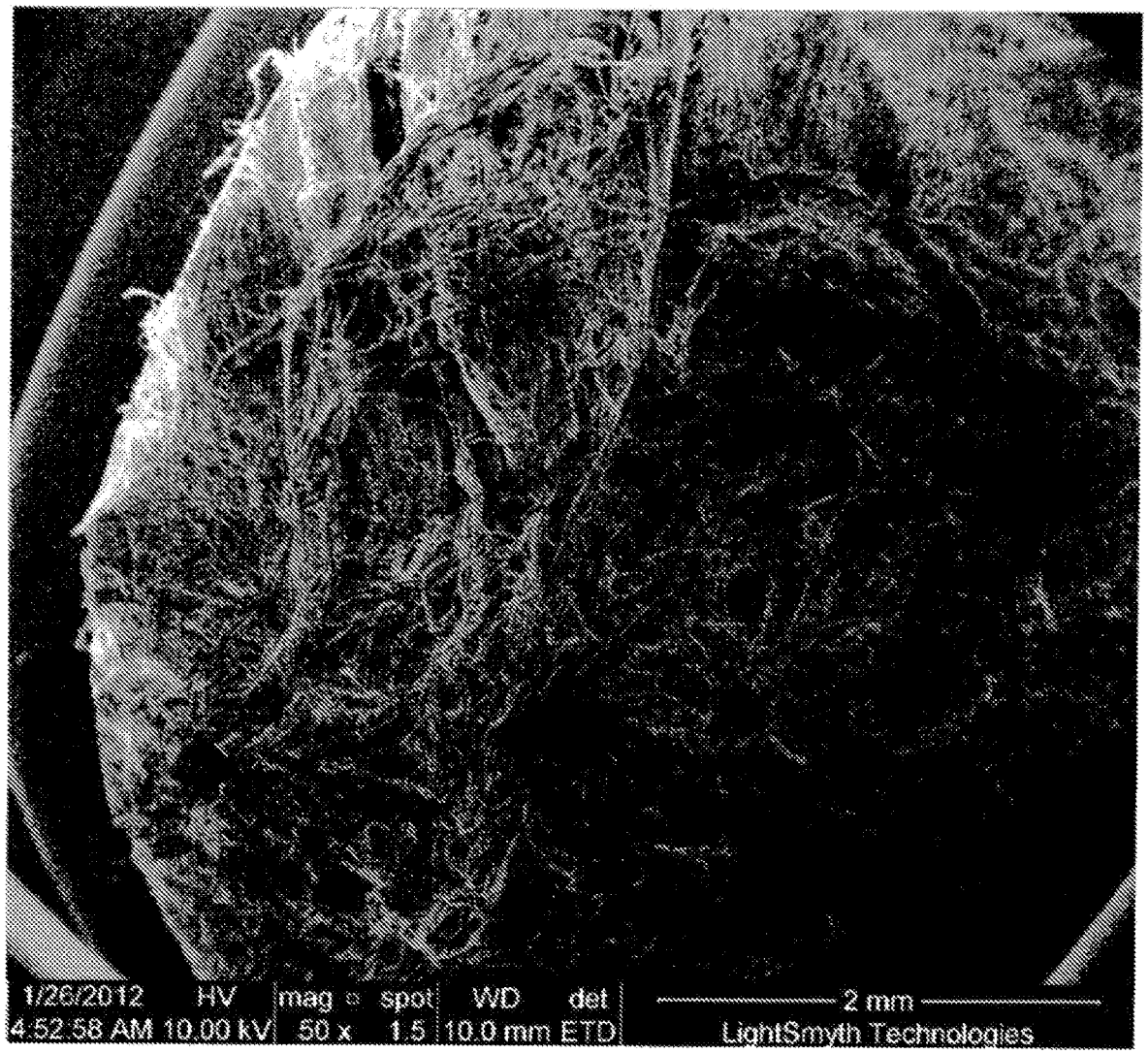
Figure 3D:
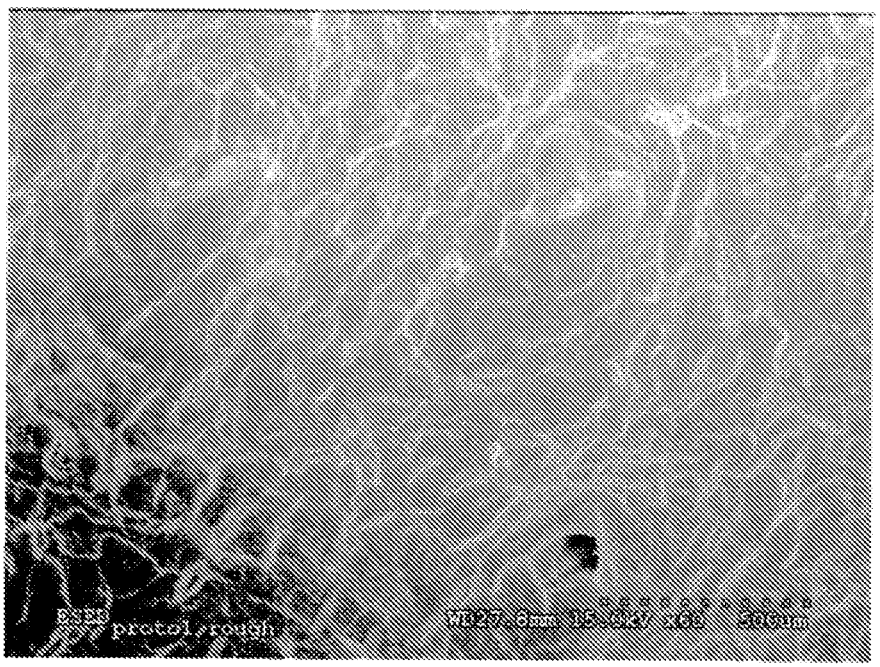
Figure 3E:
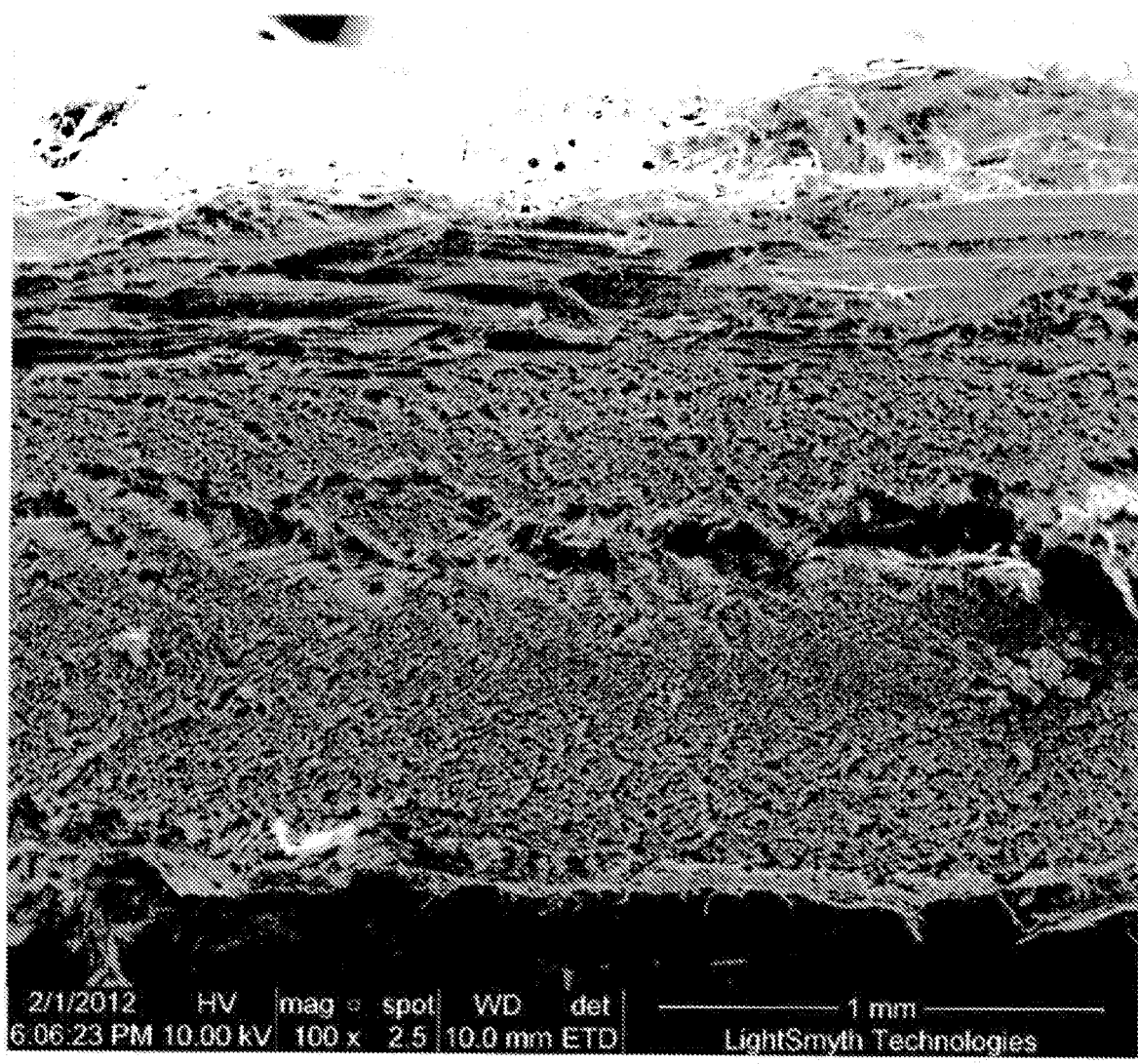
Figure 3F:
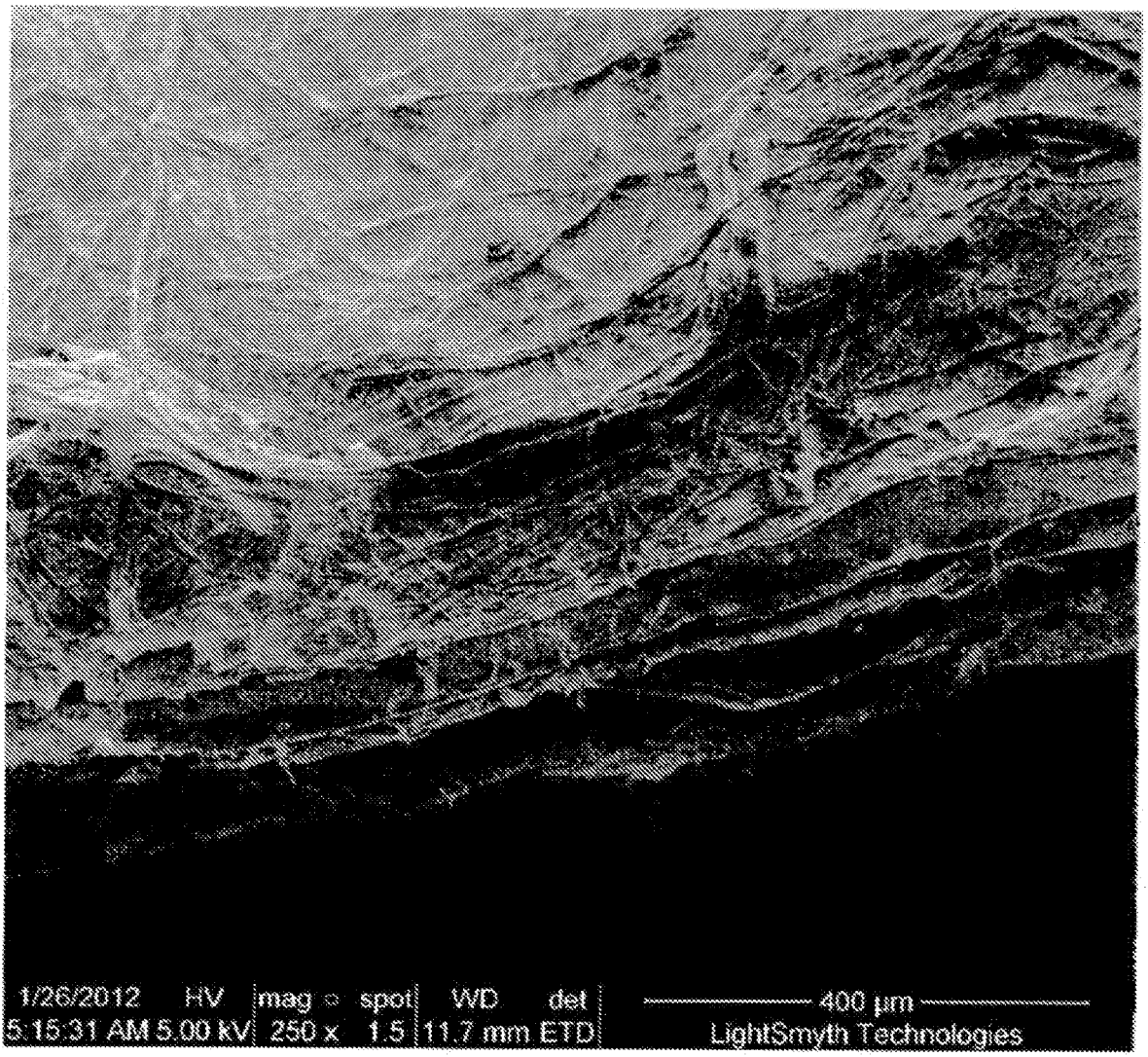
Figure 3G:
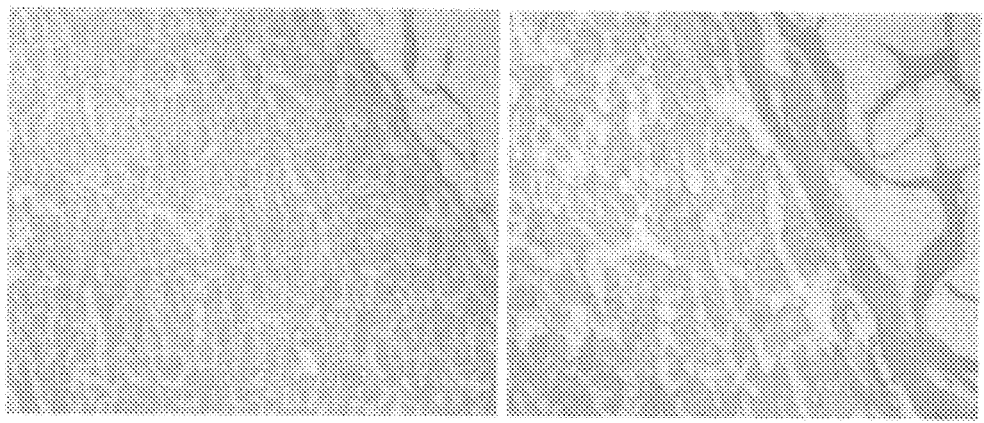

FIG. 3(a) shows a decellularized and lyophilized porcine rectus sheath fascia surface (70× magnification). The apparent porosity (open structure) is suitable for cell and tissue ingrowth. FIG. 3(b) shows a decellularized porcine rectus sheath fascia in cross section (70× magnification). The laminar and fibrous structures are shown. There are three distinct layers where each layer appears to have a separate orientation, which is consistent with the anatomical organization of rectus sheath fascia. FIG. 3(c) shows a decellularized and lyophilized bovine shoulder fascia collagen surface (50× magnification). The fibrous structure with multi-axial fiber orientation is shown. The apparent porosity is suitable for cell and tissue ingrowth. FIG. 3(d) shows a decellularized and lyophilized porcine dermis surface (60× magnification) for comparison. The lack of porosity reduces the opportunity for cell and tissue ingrowth. FIG. 3(e) shows a decellularized and lyophilized bovine shoulder fascia (100× magnification) in cross section. The fascial layers and multi-axial fiber orientation is shown. FIG. 3(f) shows a decellularized and lyophilized bovine shoulder fascia (250× magnification). The discrete layers of collagen with multi-axial fiber orientation is shown. FIG. 3(g) shows a decellularized and lyophilized bovine shoulder collagen surface (light microscope 40× and 100× magnifications). Hyalinized bands of loose connective tissue are shown. No cell nuclei are identified by light microscopy within H & E stained sections.

In certain embodiments, the biomaterial may have a plurality of pores, or open spaces between fibers. Typically, the pores or open spaces may have a variety of sizes ranging from 20 to 300 microns, or from 50 to 200 microns. Certain regions of the biomaterial may have larger pores, ranging in sizes from 100 to 300 microns that may appear as "open spaces between fibers." The pores or open spaces may aid in tissue integration thus decreasing adhesion formation, especially adhesion formation to viscera. The pores or open spaces may afford tissue ingrowth.

In certain embodiments, the biomaterial may be cross-linked or not cross-linked. The biomaterial may be cross-linked by chemical modification to make it more resistant to tearing, degradation, creep and attenuation under functional loading. In certain embodiments, the biomaterial is perforated or formed into a mesh for improved tissue grafting or integration.

In certain embodiments, the biomaterial has been processed, modified or treated to remove cells, fat, protein (e.g., non-collagenous protein), nucleic acid, non-collagenous and/or antigenic components present in the mammalian or non-human source from which the biomaterial was derived. In certain embodiments, the biomaterial has been cleaned, decellularized, de-fatted, purified and/or lyophylized.

While not intending to be bound by theory, it appears that layering the biomaterial provides the biomaterial with increased or additional strength. In certain embodiments, the biomaterial may include at least 2, 3, 4, or more layers. In certain embodiments, the biomaterial includes a plurality of biomaterial elements stitched, sutured, joined or quilted together to increase size or thickness. Such biomaterials with increased size or thickness may provide stronger augmentation materials or in larger sizes to fit a variety of clinical conditions.

In certain embodiments, the biomaterial may be combined with, treated with or formed into a multi-component, or coated, fused or layered construct, with one or more second materials. The second material may include a material that provides the biomaterial with increased or additional strength. The second material may be autologous (i.e., harvested from the recipients' own body) or may be xenograft to the recipient (i.e., harvested from a donor, e.g., of the same or different species).

The second material may comprise a synthetic or biologic hard, semi-soft or soft, flexible or rigid, mesh, implant, graft, or prosthesis. The second material may limit, prevent, and retard adhesion formation, especially adhesion formation to viscera. The second material may include an absorbable polymer mesh. The second material may include a polymer material or an absorbable layer. Exemplary polymer material that can be used in accordance with the invention includes but not limited to polyglycolide, polydioxanone, polypropylene (PP), polyester, polytetrafluoroethylene (PTFE), expanded polytetrafluoroethylene (ePTFE), polyetheyleneterephthalat (PET), and mixtures thereof. Various types of absorbable polymer mesh are commercially available including Vicryl® mesh (polylgalactin 910) or Monocryl® (polyglecaprone 25).

The second material may include tissues of a mammalian, human or non-human recipient. The second material may improve or increase integration, grafting, durability or stability of the biomaterial when integrated into or combined with tissue of a mammalian, human or non-human recipient. The second material may include mammalian cells that are autologous or are a xenograft with respect to the source of the biomaterial, or are autologous or are a xenograft with respect to the recipient of the biomaterial. The mammalian cells includes dermis cells, or stem cells, fibroblasts, myoblasts, myocytes, endothelial cells, immune cells (macrophages, monocytes), osteoblasts, or chondroblasts. In certain embodiments, the biomaterial is a xenograft with respect to a potential recipient of the material. For example, a human recipient may receive a non-human biomaterial, for example, from a donor such as a pig (porcine), cow (bovine), sheep (ovine), horse (equine), and goat (hircine).

Second materials also include factors (proteins, hormones, etc.) that promote blood vessel growth, tissue integration of the biomaterials. The second material may include an autologous or recombinant growth factor, chemokine or cytokine, such as platelet derived growth factor (PDGF), epidermal growth factor (EGF), insulin like growth factor (IGF)-1, fibroblast growth factor (FGF), transforming grow factor (TGF), such as TGF-beta. The second material may include a bone morphogenic protein (BMP), such as BMP-2, BMP-3, BMP-4, or BMP-7. In certain embodiments, the biomaterial is treated with autologous or recombinant growth factors such as PDGF, EGF, IGF-1, FGF, TGF-beta, BMP-2, BMP-3, BMP-4, BMP-7 or a combination thereof.

In certain embodiments, second materials include mitogenic agents such as autologous platelet rich plasma or allogenic platelet concentrate to enhance cell attachment, migration and wound healing. Accordingly, a biomaterial may be combined with any other second material to provide distinct, additional, or synergistic characteristics, structures or functions.

In certain embodiments, a biomaterial has a first rough side and an opposing second dense side. The first rough side may provide for cell ingrowth in a recipient. Generally, the second dense side is a more fibrous layer. The second dense side may provide for reduced cell ingrowth or adhesion to viscera or bowel of a recipient. The second dense side may include one, two, or more layers of the same or different materials. For example, the second dense side may include two or more dense layers for more demanding applications such as large hernias or abdominal wall reconstructions. The second dense side may include two or more of the less dense layers for example as a matrix for stem cell application in soft tissue repair. Thus, the biomaterial may have a dual or multi-density construct. In one embodiment, the biomaterial includes bovine, porcine or equine fascia with a more dense layer such as a dermis, for example, bovine, porcine or equine dermis.

Various techniques can be used to form the multi-layer construct of the biomaterial including but not limited to welding, joining, and gluing with an adhesive. Specifically, the layers may be joined by laser welding, continuous suturing or stitching, intermittent stitching, or gluing together with cross-linked and not cross-linked collagen based glue or other biocompatible adhesives. In certain embodiments, the biomaterial has a quilted, stitched, sutured, or attached multi-layer construct, a predominantly flat, folded or rolled sheet. In certain specific embodiments, the biomaterial is expanded by quilting, stitching, suturing or attaching together two or more biomaterial elements. In specific embodiments, two or more flat sheets may be sewn together with reinforcing rolled borders. The rolled borders serve to provide a "memory" function so that the biomaterial may be rolled into a cylinder (e.g., scroll), delivered via trocar and then spontaneously unrolled itself back into a flat sheet. The rolled borders may be obtained from the linea alba, or constructed from other tendinous of an animal such as the Achilles tendon, or rectus sheath fascia. In certain embodiments, the biomaterial can be cut or trimmed into a variety of sizes and shapes such as oval, circular, rectangular or square. The biomaterial can be cut without loss of fiber integrity or disruption of fiber orientation.

Certain embodiments of the invention provide a biomaterial that exhibit physical, structural, physical-chemical, bio-mechanical, properties suitable for use in accordance with the invention. Such physical, structural, physical-chemical, bio-mechanical, properties can be combined.

For thickness, the biomaterial may have a thickness between 0.2 mm and 5 mm, between 0.4 mm and 2.5 mm, or between 0.8 mm and 2.5 mm. In an exemplary embodiment, mean thickness was about 2.7, with a range of 2.1 to 3.4 mm. Commercially available hernia repair material ranges from 1.2 to 2.8 mm, such that the foregoing biomaterial is suitable for hernia repair and similar applications.

For suture retention strength, the biomaterial may exhibit suture retention strength of greater than 20 Newtons (N), greater than 50 N, between 4 and 150 N, between 20 and 150 N, or between 20 and 80 N. In an exemplary embodiment, mean suture retention strength was 49 with a range of 30 to 66. Commercially available hernia repair material ranges from 29-127N, such that the foregoing biomaterial is suitable for hernia repair and similar applications.

For tear resistance, the biomaterial may exhibit tear resistance of at least 5 N, between 5 and 100 N, between 10 and 90 N, or between 10 and 50 N. In an exemplary embodiment, mean tear resistance was 26N with a range of 17 to 38 N. Commercially available hernia repair material ranges from 17-85 N such that the foregoing biomaterial is suitable for hernia repair and similar applications.

For tensile strength (i.e., uniaxial or multiaxial tensile strength), the biomaterial may exhibit tensile strength of at least 20 N, or between 50 and 500 N. Alternatively or in addition, a biomaterial may have between 2 mega pascals (MPa) and 30 MPa of tensile strength.

For ball burst tensile strength, the biomaterial may exhibit a ball burst tensile strength of at least 50 N/cm, between 50 and 1200 N/cm, or between 60 and 1100 N/cm. In an exemplary embodiment, mean ball burst tensile strength was 188 N/cm with a range of 100-286 N/cm. Commercially available hernia repair available material ranges from 271 to 1028 N/cm such that the foregoing biomaterial is suitable for hernia repair and similar applications.

For ball burst maximum load, the biomaterial may exhibit ball burst maximum load of 700 N, with a range of 400 to 1200 N.

For ball burst strain (a measurement of the percentage of stretch at a stress of 16N/cm), the biomaterial may exhibit ball burst strain (stretch) of at least 10%, at least 20%, between 5% and 35%, between 10% and 30%, or between 10% and 20%. In an exemplary embodiment, mean ball burst strain (at a stress of 16N/cm) was 15% with a range of 9 to 25%. Commercially available hernia repair ball burst strain ranges from 10 to 26% such that the foregoing biomaterial is suitable for hernia repair and similar applications.

Typically, the biomaterial exhibits comparable or better ball burst tensile strength, for exampe, in terms of Maximun Load, and/or Tensile Strength at Burst and Strain than other collagen products (see, e.g., Deeken et al., "Differentiation of biologic scaffold materials through physicomechanical, thermal, and enzymatic degradation techniques;" Annals of Surgery, e-publication. Feb. 4, 2012).

In certain embodiments, a method for manufacture of hernia implant comprises forming at least two independent structures, one biologic and one synthetic and joining structures to form a composite flexible structure.

The biomaterial include materials that are stable under conditions used for sterilization, for example, with gamma or electron beam radiation, and additionally are stable on storage and in the course of delivery. The biomaterial is usually packaged in a sterile double package prior to delivery to sterilization.

In accordance with the invention, methods and uses of repair or augmentation of a tissue, such as a soft or a hard tissue, are provided. In certain embodiments, the tissue includes congenitally attenuated, damaged or injured tissue as a result of deformity, disease or trauma. In certain embodiments, the repaired or augmented tissue is abdomen, abdominal wall or muscle.

In one embodiment, a method and use for repair or augmentation of a tissue of a recipient mammalian subject in need of repair or augmentation, includes attaching, joining or affixing thereto a biomaterial described herein to the tissue of the recipient mammlian subject in need of repair or augmentation.

In certain embodiments, a biomaterial for a recipient can be a xenograft or allograft biomaterial. As used herein, the term "xenograft," refers to tissue transferred from one subject of one species to a recipient of another species. As used herein, the term "allograft," refers to tissue transferred from one subject of one species to a recipient of the same species ("allogeneic"). With respect to soft tissue for xenografts, porcine, bovine, ovine, equine or hircine can be harvested to form xenografts or allografts according to procedures known to those of ordinary skill in the art.

In one embodiment, a method and use for closure or repair of a wound or cavity in a tissue of a recipient mammlian subject, includes a) providing a biomaterial described herein; b) contacting the wound with the biomaterial, or positioning, shaping or contouring the biomaterial over the cavity, or introducing the biomaterial into the cavity; c) joining, attaching or affixing the biomaterial to the wound or cavity to secure said biomaterial; and d) closing said cavity or repairing said wound in the tissue.

In one embodiment, a method and use of repairing a defect or augmenting a tissue of a recipient mammlian subject in need thereof, includes a) positioning, shaping or contouring the biomaterial described herein to cover a defect or augment the tissue in need thereof; and b) securing the biomaterial in place.

In one embodiment, a method and use for tissue repair or augmentation includes delivering to tissue of a recipient mammlian subject a biomaterial described herein, wherein the biomaterial serves to repair or augment the tissue. In a further embodiment, the biomaterial is delivered through small entrances such as laparoscopic ports, or large incisions to tissue of a recipient mammlian subject. In a specific embodiment, the biomaterial is delivered to tissue of a recipient mammlian subject according to a laparoscopic surgical procedure.

Figure 4:
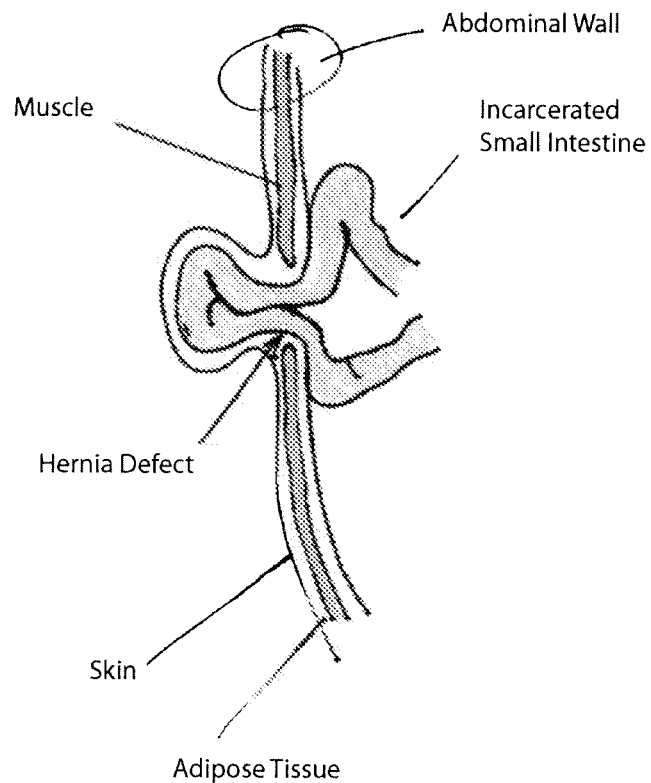
FIG. 4 shows a saggital section of a pre-laparascopic hernia repair view of an abdominal wall with bowel incarcerated in hernia defect according to embodiments of the invention.
Figure 5:
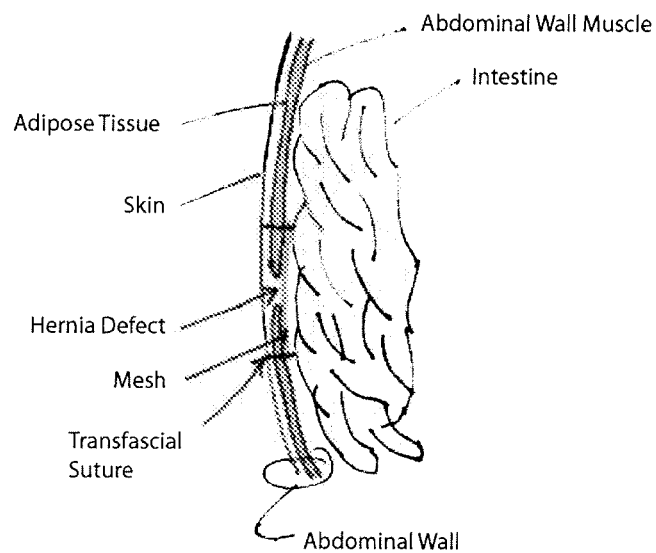
FIG. 5 shows a saggital section of a post-laparascopic hernia repair view of a small intestine withdrawn from the abdominal wall defect with subsequent coverage of the defect utilizing the invention.
Figure 6:
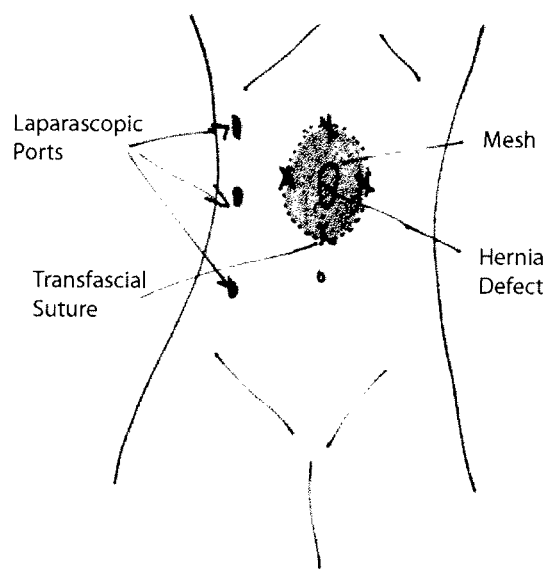
FIG. 6 shows a post-laparascopic hernia repair view illustrating the biomaterial has been surgically secured to the abdominal wall and covering the hernia defect according to the invention.

A saggital view of incarcerated small intestine being trapped within an abdominal wall defect (hernia defect) is illustrated in FIG. 4. The incarcerated small intestine is withdrawn from the hernia defect according to a laparoscopic surgical procedure. A diagramatic representation of a sagittal view of a small intestine withdrawn from the abdominal wall defect with subsequent coverage of the defect utilizing the methods and uses of the invention is illustrated in FIG. 5. A diagramatic representation of a post-laparascopic hernia repair view illustrating the biomaterial has been surgically secured to the abdominal wall and covering the hernia defect is illustrated in FIG. 6. The figure also shows the location of the laparascopic ports.

Recipient mammalian subjects may be any mammalian species, such as but not limited to human, dog, cat, horse, pig, and sheep. The recipient mammlian subject may have an abdominal wall defect, trauma, damage, or weakness, a hernia, a fistula, or torn or damaged dura, or an orthopedic defect trauma, damage, or weakness (e.g., damaged or injured ligament or tendon). In one embodiment, the recipient mammlian subject is suffering from a hernia, such as a ventral incisional hernia; a umbilical, inguinal, femoral, spigelian, parastomal or hiatal hernia; a diaphragmatic hernia; and a lumbar triangle hernia.

In certain embodiments, the recipient mammlian subject is in need of pelvic floor reconstruction; in need of repair, reinforcement or augmentation of esophageal perforations or defects; in need of a protective barrier between vascular anastamosis and bowel; in need of a protective barrier between viscera following repair; in need of correction or surgery for rectal prolapse; in need of maxillofacial, periodontal or dental surgery: as a soft tissue augmentation material or in the repair of hard and/or soft tissue defects; in need of skeletal defect repair; in need of orthopedic surgery; in need of urologic surgery; in need of gynecologic surgery; in need of plastic surgery; or in need of neurosurgery.

In certain embodiments, the recipient mammlian subject is in need of a protective barrier between vascular anastamosis (i.e., proximal aortic anastamosis) and bowel (i.e., duodenum) as encountered following aortic reconstruction utilizing prosthetic vascular grafts; in need of a protective barrier between viscera following repair of rectovaginal fistula, rectovesicle fistula; in need of skeletal defect repair in the craniomaxillofacial or axial skeleton; in need of orthopedic surgery for joint repair or replacement or in soft tissue repair or augmentation of joints or to reinforce, augment, replace weakened, injured, attenuated or diseased ligamentous, tendinous or joint structures; in need of urologic surgery for stress urinary incontinence or organ prolapse (e.g., rectal prolapse); in need of gynecologic surgery to correct or reinforce for pelvic floor weakness, as in rectocele, cystocele, vaginal prolapse; in need of plastic surgery to support or reinforce, inhibit or limit migration of implanted prosthesis, reinforce or augment defects or areas of weakness created by mobilization of soft tissues used in various reconstructive procedures, or to create, alter or manipulate body contours; or in need of neurosurgery for dural replacement and/or patch of a dural defect.

Methods and uses of the invention can be practiced with respect to all variations of biomaterials set forth herein. For example, in some embodiments, the biomaterial is a xenograft with respect to the recipient mammalian subject. In other embodiments, the biomaterial is an allograft with respect to the recipient mammalian subject. For example, the biomaterial is a decellularized and/or lyophyized xenograft or allograft with respect to the recipient mammalian subject. In certain embodiment, the biomaterial may further include cells or proteins that are allogeneic or autologous with respect to the recipient mammalian subject.

Certain embodiments of the invention provides methods for manufacturing biomaterials suitable for tissue repair or augmentation includes (a) obtaining a multi-layered, naturally occurring multi-axial oriented biomaterial comprising predominately type I collagen fibers; and (b) processing, modifying or treating the biomaterial to be suitable as a xenograft in human and non-human mammal tissue repair or augmentation.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described herein.

All applications, publications, patents and other references cited herein are incorporated by reference in their entirety. In case of conflict, the specification, including definitions, will control.

As used herein, the singular forms "a", "and," and "the" include plural referents unless the context clearly indicates otherwise.

As used herein, numerical values are often presented in a range format throughout this document. The use of a range format is merely for convenience and brevity and should not be construed as an inflexible limitation on the scope of the invention. Accordingly, the use of a range expressly includes all possible subranges, all individual numerical values within that range, and all numerical values or numerical ranges including integers within such ranges and fractions of the values or the integers within ranges unless the context clearly indicates otherwise. This construction applies regardless of the breadth of the range and in all contexts throughout this document. Thus, for example, reference to a range of 10-30% includes 10-13%, 11-14%, 12-15%, 13-16%, 10-20%, 11-25%, 15-25%, 20-25%, 25-30%, and so forth. Reference to a range of 10-30% also includes 11%, 12%, 13%, 14%, 15%, 16%, 17%, etc., as well as 11.1%, 11.2%, 11.3%, 11.4%, 11.5%, etc., 12.1%, 12.2%, 12.3%, 12.4%, 12.5%, etc., and so forth.

In addition, reference to a range, for example, of 4-150 N (e.g., suture retention strength) includes 4, 5, 6, 7, 8, 9, 10, . . . 146, 147, 148, 149, and 150 as well as 4.1, 4.2, 4.3, 4.4, 4.5, etc., 5.1, 5.2, 5.3, 5.4, 5.5, etc., 149.1, 149.2, 149.3, 149.4, 149.5, and any numerical range within such a ranges, such as 4-10, 4-50, 10-30, 10-60, 10-140, 80-130, 80-140, 80-150, etc. In a further example, reference to a range of 4-150 N, includes without limitation 10-20, 20-30, 30-40, 40-50, 50-60, 60-75, 75-100 N, and any numerical value or range within or encompassing such values.

As also used herein a series of ranges are disclosed throughout this document. The use of a series of ranges includes combinations of the upper and lower ranges to provide another range. This construction applies regardless of the breadth of the range and in all contexts throughout this document. Thus, for example, reference to a series of ranges such as between 5% and 35%, between 10% and 30%, and between 10% and 20%, includes ranges such as 5-30%, 5-35%, 5-20%, 10-35%, 5-10%, and so forth.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example describes a biomaterial suitable for tissue repair or augmentation.

A section of porcine abdominal wall was harvested from a market-size pig in a USDA inspected facility. The animal was certified for human consumption and further inspected and certified as such by a veterinarian. The entire abdominal wall was harvested by means of a wide, full-thickness circular incision from the costal margins superiorly to the pelvic region inferiorly, harvesting as much tissue as possible and extending posteriorly to the spine. No midline incision was made to preserve the integrity of the rectus sheath. The tissue was transported to an appropriate facility where it was washed thoroughly using room temperature water. The skin and superficial fat was removed by mechanical means using sharp and blunt dissection, and the tissue was washed again with running deionized water. The tissue was disinfected in 0.5% sodium hypochlorite solution, and it was frozen for shipping and storage. Alternatively, to avoid the freezing step, the tissue may be placed into a solution containing a protease inhibitor and an antibiotic. Examples of appropriate protease inhibitors includes ethylenediaminetetracetic acid (EDTA) in concentrations of 1-15 mM or 0.2 mM phenymethylsulfonyl flouride (PMSF). Examples of appropriate antibiotics includes solutions such as Penicillin, Gentamycin or Vancomycin.

To harvest the fascial layers, the tissue was first allowed to slowly thaw at 20 to 25° C., and additional cleaning and dissection was carried out until the fascial layer overlying the external oblique was visualized. Using blunt and sharp dissection, the fascial layer (multi-laminar and multi-directional) was isolated and cleaned, and as much superficial fat was removed as possible. Dissection was carried out laterally to the medial borders of the oblique muscles and superiorly and inferiorly to the borders of the tissue. Once the rectus abdominis muscles were identified, a small incision was made bilaterally on the lateral border of the muscle, and the muscle was separated from the fascial layers anteriorly and posteriorly using a combination of blunt and sharp dissection such that the muscle was removed in its entirely from the fascial layers. The fascial tissue was then further treated to remove fat, non-collagenous proteins, blood vessels and cells, leaving behind a clean, predominately type I collagen multilayered membrane.

To begin the decellularization process, the tissue was rinsed under running water, and then immersed in a dilute solution of sodium hypochlorite for 15 minutes. Chemical de-fatting was carried out by dehydrating the tissue in 100% ethanol for 10 minutes, followed by rotary agitation in a mixture of hexane (70%) and acteone (30%) for 24 hours. The tissue was rinsed with 100% ethanol for 10 minutes, and then with 70% ethanol for 10 minutes. The rinsed tissue was placed in deionized water for 1 hour. The water was changed and the tissue was rinsed for an additional two 1-hour cycles using rotary agitation at 200 RPM. Decellularization was accomplished by placing the tissue in a solution of 1% Triton X-100 in phosphate buffer with 1% EDTA for 24 hours using rotary agitation at 200 RPM. After the first 2 hours, the solution was exchanged for fresh solution, soaked for 4 hours and exchanged again after 12 hours. The tissue was then washed again in DI water for three 1-hour cycles. The tissue was then placed in 1% sodium dodecyl sulphate (SDS) in phosphate buffer for 24 hours using rotary agitation at 200 RPM. It was then rinsed in DI water, using three 1-hour cycles and then placed into phosphate buffer for 1 hour. Lyophylization was carried out by placing the wet tissue onto stainless steel trays and placing into a lab scale freeze dryer. Lyophylization was initiated by freezing with a shelf temperature set to −40° C. and the product was held for 120 minutes at a pressure 300 millitorr (mtorr). The temperature was ramped to −20° C. and the pressure was decreased to 50 mtorr over 180 minutes. Next, over the next 400 minutes the temperature was ramped to 15° C. at 50 mtorr and then to 20° C. and 50 mtorr over the next 1200 minutes. Next, the temperature was increased to 30° C. and held for 30 minutes at which time the cycle was terminated. The freeze dryer was then vented with room air and the product was promptly removed from the lyophylizer and sealed in polyethelyene bags for storage.

Example 2

This example describes an exemplary biomaterial from bovine shoulder fascia.

A section of bovine shoulder fascia was harvested from a market-size calf in a USDA inspected facility. The animal was certified for human consumption and further inspected and certified as such by a veterinarian. The shoulder fascia was harvested by careful dissection of the thick layer of fascia overlying the deltoid, trapezius and omo-brachialis region after the skin and superficial fat are removed. The tissue was disinfected in mild sodium hypochlorite solution and frozen for shipping and storage.

To begin processing, the tissue was slowly thawed and additional cleaning and dissection of fat and loose connective tissue was carried out until the distinct fascial layers were visualized. Using blunt and sharp dissection, this complex multi-laminar, multi-directional layer was isolated and cleaned, removing as much superficial fat as possible.

Next, the tissue was rinsed under running, pyrogen-free water, then immersed in a dilute solution of 0.5% sodium hypochlorite. The tissue was then placed into a 1 L jar containing 950 ml of 1% Triton X-100. The jar was placed on a rotary shaker for 24 hours. The tissue was rinsed DI water using rotary shaking three times for 30 minutes. The rinsed tissue was placed into a phosphate buffer solution for 30 minutes, then placed into a solution of 2% lipase for 8 hours at pH 8.5. The tissue was then rinsed in deionized water for two 1-hour cycles using rotary agitation, then placed again into the phosphate buffer for 30 minutes. Additional de-fatting was carried out by placing the tissue in a 1 L jar of 70% ethanol with rotary agitation at 200 RPM for 24 hours followed by a 1 hour rinse with deionized water. A second detergent step was then done using 0.5% SDS in phosphate buffer at pH 7.5 for 24 hours at 200 RPM. The tissue was again rinsed in DI water using two 1 hour cycles and then immersed in phosphate buffer for 30 minutes.

Lyophylization was carried out in a laboratory scale freeze-dryer. The product was placed wet on a stainless steel tray and frozen using an initial shelf temperature was −40° C. and held at atmospheric pressure for 120 minutes. The temperature was slowly ramped to 5° C. at a pressure of 100 mtorr over a period of 400 minutes, then increased to 15° C. and over a period of 400 minutes at 100 mtorr, then increased to 20° C. over a period of 400 minutes at 100 mtorr, then increased to 25° C. over 120 minutes at 100 mtorr, then increased to 30° C. over a period of 40 minutes at 100 mtorr. The lyophylizer was then vented to room air and the cycle was terminated. The product was promptly removed from the chamber in sealed in Tyvek bags for storage.

Example 3

This example describes mechanical testing of an exemplary Bovine Fascia Biomaterial.

The physicomechanical properties of a collagen-based exemplary biomaterial for hernia repair was evaluated using various means of mechanical testings described below to determine the suitability for hernia repair application. These tests were performed as described (Deeken et al., "Differentiation of biologic scaffold materials through physicomechanical, thermal, and enzymatic degradation techniques;" Annals of Surgery, e-publication. Feb. 4, 2012).

Figure 7:
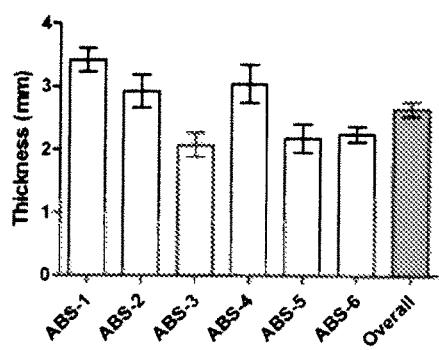
FIG. 7 shows thickness measurements of an exemplary bovine fascia biomaterial according to the invention by a laser micrometry.

Exemplary scaffolds (biomaterials) were prepared according to the process described in Example 2 herein. Thickness of the biomaterial is indicated in FIG. 7.

A. Laser Micrometry

The thickness of six scaffolds (biomaterials) was measured using an LK-081 digital laser micrometer and LK-2101 controller (Keyence, Woodcliff Lake, N.J.). The thickness of each scaffold was measured nine times (n=9) and was reported as mean±standard error of the mean (SEM). The results of the laser micrometry test are shown in FIG. 7.

Substantial variability was observed both between different scaffolds of one embodiment of the biomaterial, i.e., acellular bovine shoulder (ABS), and between different regions within the same embodiment of the ABS biomaterial.

B. Biomaterial Suture Retention Strength

Figure 8:
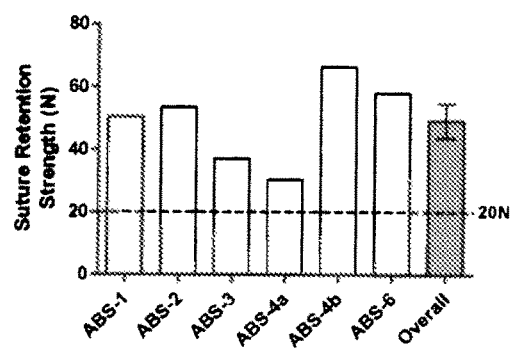
FIG. 8 shows suture retention strength measurements of an exemplary bovine fascia biomaterial according to the invention.

Six scaffolds (n=6) measuring 2.5×5.1 cm (1×2 inches) were prepared. A custom test fixture was utilized in which the scaffold was loaded with a gauge length of 2.5 cm (1 inch) and clamped along the upper edge using pneumatic grips set to 60 psi. A stainless steel wire with a diameter of 0.36 mm was passed through the scaffold 1.0 cm from the bottom edge. Polypropylene suture (e.g. size "0" suture) has a diameter of 0.35 mm. Thus, the diameter of the wire was chosen to replicate this type of suture as closely as possible. Each scaffold was tested in tension at a rate of 300 mm/min (12 in/min) until the suture tore out of the scaffold. The suture retention strength was recorded as the maximum load sustained by the scaffold in units of Newtons (N) and is reported as mean±SEM. The results of the suture retention strength test are shown in FIG. 8.

All of the scaffolds (biomaterials) individually demonstrated suture retention strengths exhibit greater than 20N as suggested for hernia repair applications (de Vries Reilingh et al, "Autologous tissue repair of large abdominal wall defects," Br J Surg. 2007 July; 94(7):791-803, and Deeken et al, (2010) "Physicomechanical evaluation of absorbable and nonabsorbable barrier composite meshes for laparoscopic ventral hernia repair," Surg Endosc 2010; 25: 1451-1552). The overall average of all six ABS scaffolds also demonstrated suture retention strength greater than the 20N value suggested for hernia repair applications.

C. Biomaterial Tear Resistance

Figure 9:
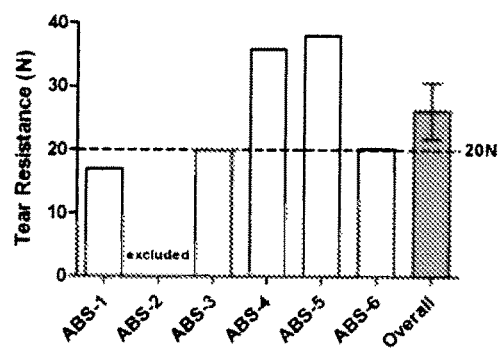
FIG. 9 shows tear resistance measurements of an exemplary bovine fascia biomaterial according to the invention.

Tear resistance testing (based on the ASTM specification # D2261-07a) was performed. Six scaffolds (n=6) were prepared measuring 2.5×7.6 cm (1×3 inches). A 2.5 cm (1 inch) slit was cut from the midline of the 2.5 cm edge of the scaffold toward the center of the scaffold to form two tabs or "pant legs". The left tab was clamped in the upper grip using a pneumatic grip set to 60 psi, and the right tab was clamped in an identical fashion in the lower grip. Such arrangement yielded a 2.5 cm gauge length (1 inch). The test was conducted in tension at a rate of 300 mm/min (12 in/min) until the scaffold tore in half. The "tear strength" was recorded as the maximum load sustained by the scaffold in units of Newtons (N) and is reported as mean±SEM. The results of the tear resistance test are shown in FIG. 9.

All of the exemplary scaffolds (except ABS-1) individually demonstrated tear resistance strengths greater than the 20N value suggested for hernia repair applications. The overall average of five ABS scaffolds (ABS-2 excluded from the analysis) also demonstrated tear resistance strength greater than the 20N value suggested for hernia repair applications.

D. Ball Burst

Six scaffolds (n=6) measuring 7.5×7.5 cm (3×3 inches) were prepared for burst testing.

Figure 10A:
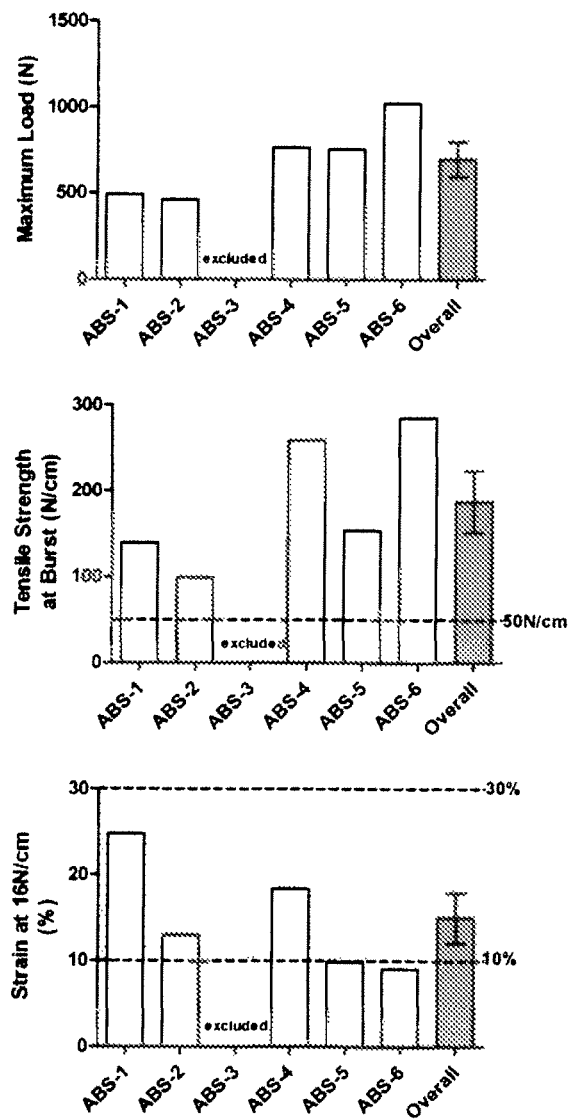

A custom test fixture was fabricated based on ASTM specification # D3787-07. Two circular grooved stainless steel plates were utilized to clamp the scaffold (biomaterial) to prevent slipping during the test. A 2.5 cm diameter (1 inch) stainless steel ball was applied in compression at a rate of 300 mm/min (12 in/min) until it burst through the scaffold. The ultimate tensile stress and the strain at a stress of 16N/cm (i.e., the extent of stretch) were recorded in units of N/cm and percent respectively and are reported as mean±SEM. The results of the ball burst test are shown in FIGS. 10(a) and (b).

All of the scaffolds individually demonstrated ball burst tensile strengths greater than the 50N/cm value suggested for hernia repair applications. The overall average of five ABS scaffolds (ABS-3 excluded from the analysis) also demonstrated ball burst tensile strength greater than the 50N/cm value suggested for hernia repair applications.

All of the scaffolds (except ABS-6) individually demonstrated ball burst strain values in the suggested range of 10-30% for hernia repair applications. The overall average of five ABS scaffolds (ABS-3 excluded from the analysis) also demonstrated ball burst strain value in the suggested range of 10-30% for hernia repair applications.

Example 4

This example describes exemplary non-limiting applications of biomaterials of the invention.

After induction of general anesthesia to a patient, the abdomen is prepped and draped in sterile fashion. Those of skill in the art may carry out the procedure either laparoscopically or through an open approach. A variety of techniques and modifications of either approach are also intended.

Laparoscopic Approach

Figure 11A:
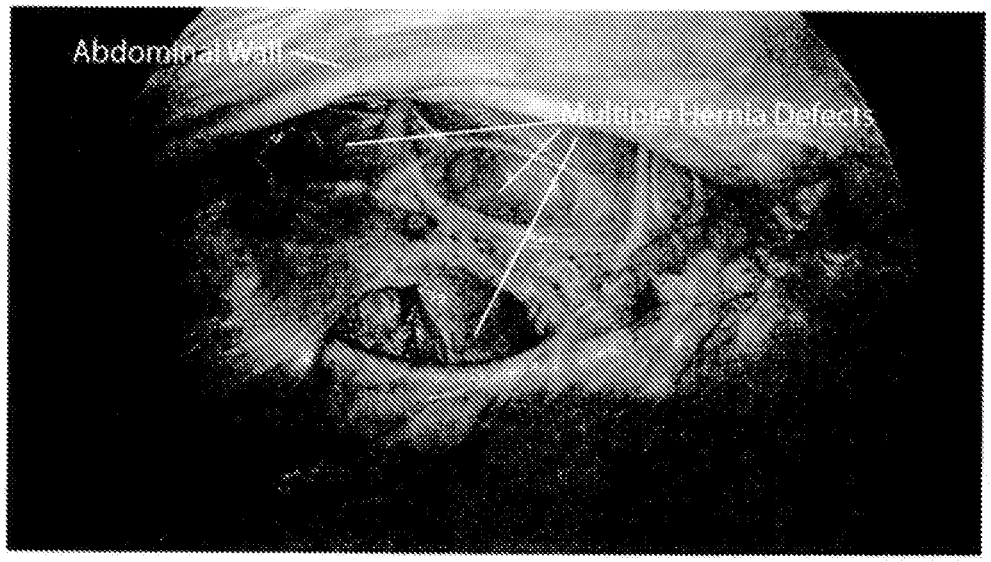
FIG. 11(a) shows an image of a pre-repair of a hernia defect according to the invention.
Figure 11B:
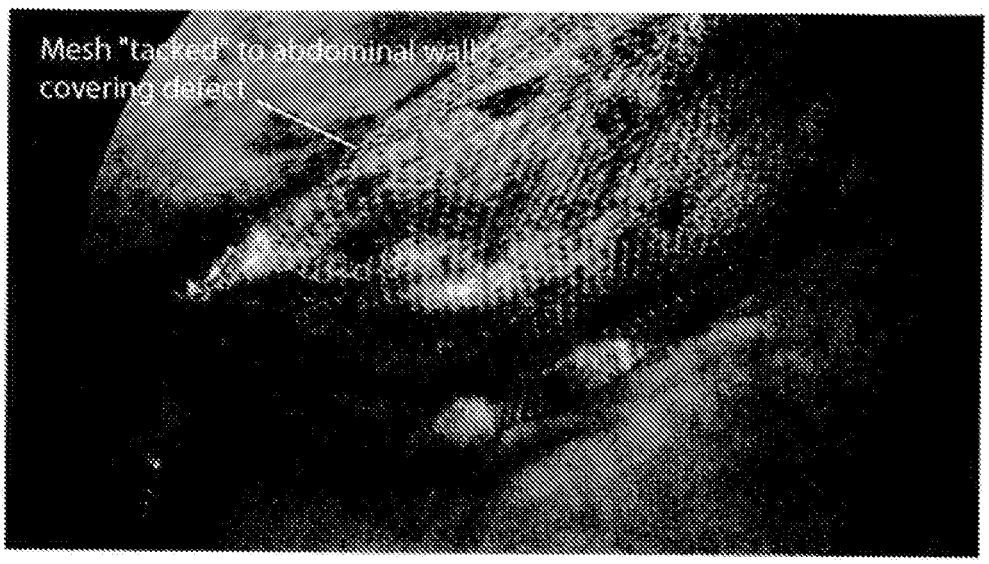
FIG. 11(b) shows an image of a post-repair of a hernia defect according to the invention.

The peritoneal cavity is insufflated with $CO_2$ and the appropriate trocars/ports are inserted laterally to gain entrance into the peritoneal cavity. The anterior abdominal wall is examined. Any adherent bowel or omentum is dissected free utilizing sharp dissection or the Harmonic Scalpel, allowing adequate visualization of the hernia defects. FIG. 11(a) shows an image of a pre-repair of hernia defect. The appropriate size and shape biologic mesh is rolled up and introduced into the peritoneal cavity through one of the trocars/ports. Subsequently, the mesh is unrolled and appropriately oriented, which is placed against the anterior abdominal wall in such a fashion that the hernia defect(s) is/are covered and overlapped by about 3-5 cm. The mesh is secured to the abdominal with transfascial sutures at "12, 3, 6 and 9 o'clock" positions, or by means of a Gra-nee Needle. The mesh is then further secured, between the sutures, at approximately 1 cm intervals, using an endotacking device. FIG. 11(b) shows an image of a post-repair of hernia defect. The $CO_2$ is evacuated, the trocars/ports are removed, trocar/port sites are sutured, and anesthesia is terminated.

Open Approach

An incision is made over the hernia defect and carried down until the abdominal wall fascia is encountered. The hernia sac is carefully opened, and any incarcerated contents reduced. Adhesions involving the abdominal wall are divided circumferentially. The appropriate size and shape mesh is then circumferentially secured to the peritoneum and posterior aspect (posterior fascia) of the anterior abdominal wall with a running suture, approximately 3 cm from the edge of the defect.

What is claimed is:

1. A method for manufacture of a biomaterial suitable for tissue repair or augmentation, comprising:
    selecting naturally-occurring muscular fascia comprising multi-layered, multi-axial oriented biomaterial that mimics composition and structure of tissue to be repaired or augmented, wherein the muscular fascia includes type I collagen fibers;
    configuring the selected muscular fascia to provide a multiaxial tensile strength of at least 20 N/cm; and
    chemically adding crosslinks to one or more layers of the muscular fascia to obtain a crosslinked biomaterial that mimics a mechanical characteristic of the tissue to be repaired or augmented, wherein the selected muscular fascia includes type I collagen fibers within each layer that are axially aligned in different directions from other type I collagen fibers within the each layer,
    wherein the muscular fascia is a xenograft with respect to a recipient of the biomaterial.

2. The method of claim 1, wherein the type I collagen fibers are oriented in three separate and distinct directions and provide the multiaxial tensile strength of at least 20 N/cm in the three separate and distinct directions.

3. The method of claim 1, wherein the naturally occurring multi-axial oriented biomaterial comprises multiple layers of tendinous, aponeurotic fibrous collagen.

4. The method of claim 1, wherein the tissue to be repaired or augmented comprises a connective tissue or abdominal wall, and wherein the alignment of collagen fibers in the muscular fascia mimics naturally oriented fibers of the abdominal wall.

5. The method of claim 1, further comprising:
removing cells, fat, protein, nucleic acid, non-collagenous and/or antigenic components from the muscular fascia to obtain a multi-density construct.

6. The method of claim 1, further comprising:
perforating the muscular fascia.

7. The method of claim 1, further comprising:
chemically adding crosslinks between two or more layers of the muscular fascia by chemical modification.

8. The method of claim 1, further comprising:
combining the muscular fascia with a second material to obtain a multi-layer construct having at least two layers.

9. The method of claim 8, wherein the multi-layer construct has at least three layers, including a layer comprising a synthetic mesh configured to provide the biomaterial with increased or additional strength.

10. The method of claim 8, wherein the second material comprises cells that are autologous with respect to the recipient of the biomaterial.

11. The method of claim 1, further comprising:
configuring a plurality of pores in the muscular fascia, wherein the pores are configured to aid in tissue grafting or integration or reducing or decreasing adhesion formation.

12. The method of claim 1, further comprising:
introducing an autologous or recombinant growth factor, chemokine, cytokine or a bone morphogenic protein to the biomaterial suitable for tissue repair or augmentation.

13. A biomaterial comprising:
muscular fascia comprising multiple layers of naturally-occurring type I collagen fibers configured to provide a multiaxial tensile strength of at least 20 N/cm and adapted to mimic composition and structure of tissue to be repaired or augmented and to mimic a mechanical property of the tissue to be repaired or augmented,
wherein the muscular fascia is a xenograft with respect to a recipient of the biomaterial,
wherein one or more layers of the muscular fascia include chemically added crosslinks, and wherein the muscular fascia includes type I collagen fibers within each layer that are axially aligned in different directions from other type I collagen fibers within the each layer.

14. The biomaterial of claim 13, wherein the muscular fascia is derived from a multi-layered, naturally occurring biomaterial comprising predominately type I collagen fibers that have multi-axial orientation.

15. The biomaterial of claim 14, wherein the naturally occurring multi-axial oriented biomaterial comprises multiple layers of tendinous, aponeurotic fibrous collagen.

16. The biomaterial of claim 13, wherein the muscular fascia is adapted to mimic a connective tissue or abdominal wall.

17. The biomaterial of claim 16, wherein the alignment of collagen fibers in the muscular fascia mimics naturally oriented fibers of the abdominal wall.

18. The biomaterial of claim 13, wherein the muscular fascia comprises a multi-density construct derived from rectus sheath fascia, from which cells, fat, protein, nucleic acid, non-collagenous and/or antigenic components have been removed.

19. The biomaterial of claim 13, wherein the muscular fascia is perforated.

20. The biomaterial of claim 13, wherein crosslinks are provided between two layers of the muscular fascia by chemical modification.

21. The biomaterial of claim 13, further comprising:
a second material provided as a third layer in a multi-layer construct that includes at least two layers of the muscular fascia,
wherein second material provides the biomaterial with increased or additional strength, and
wherein the second material comprises a synthetic mesh, graft, or prosthesis.

22. The biomaterial of claim 13, further comprising:
a second material that includes cells that are autologous with respect to the recipient of the biomaterial.

23. The biomaterial of claim 13, further comprising:
a plurality of pores configured to aid in tissue grafting or integration or reducing or decreasing adhesion formation.

24. The biomaterial of claim 13, further comprising:
an autologous or recombinant growth factor, chemokine, cytokine or a bone morphogenic protein.

* * * * *